US012797238B2

(12) United States Patent
Nahum et al.

(10) Patent No.: US 12,797,238 B2
(45) Date of Patent: Nov. 17, 2026

(54) INTRAOPERATIVE OPHTHALMIC TISSUE MONITORING DEVICE, SYSTEM AND METHOD

(71) Applicants: MOR RESEARCH APPLICATIONS LTD., Ramat Gan (IL); A.Y.Y.T—TECHNOLOGICAL APPLICATIONS AND DATA UPDATE LTD., Holon (IL)

(72) Inventors: Yoav Nahum, Ramat Gan (IL); Amir Handelman, Holon, IL (US)

(73) Assignees: MOR RESEARCH APPLICATIONS LTD., Ramat Gan (IL); A. Y.Y.T—TECHNOLOGICAL APPLICATIONS AND DATA UPDATE LTD, Holon (IL)

(*) Notice: Subject to any disclaimer, the term of this patent is extended or adjusted under 35 U.S.C. 154(b) by 479 days.

(21) Appl. No.: 18/009,806

(22) PCT Filed: Jun. 23, 2021

(86) PCT No.: PCT/IB2021/055545
§ 371 (c)(1),
(2) Date: Dec. 12, 2022

(87) PCT Pub. No.: WO2021/260576
PCT Pub. Date: Dec. 30, 2021

(65) Prior Publication Data

US 2023/0218438 A1 Jul. 13, 2023

Related U.S. Application Data

(60) Provisional application No. 63/042,840, filed on Jun. 23, 2020.

(51) Int. Cl.
*A61F 9/007* (2006.01)
*A61B 17/00* (2006.01)

(52) U.S. Cl.
CPC ............................. *A61F 9/00745* (2013.01); *A61B 2017/00022* (2013.01); *A61B 2017/00084* (2013.01);
(Continued)

(58) Field of Classification Search
CPC ........... A61B 2017/00022; A61B 2017/00084; A61B 2017/00115; A61B 2017/00119;
(Continued)

(56) References Cited

U.S. PATENT DOCUMENTS

| | | | | |
|---|---|---|---|---|
| 5,279,547 A | | 1/1994 | Costin | |
| 5,375,595 A | * | 12/1994 | Sinha | A61B 3/165 600/402 |

(Continued)

FOREIGN PATENT DOCUMENTS

| | | | |
|---|---|---|---|
| CN | 102652005 B | 6/2014 | |
| DE | 102009053208 A1 | 8/2011 | |

(Continued)

OTHER PUBLICATIONS

Igarashi T., et al., "Hydrogen Prevents Corneal Endothelial Damage in Phacoemulsification Cataract Surgery," Scientific Reports, Aug. 8, 2016, 6:31190, DOI: 10.1038/srep31190.

(Continued)

*Primary Examiner* — Christina C Lauer
(74) *Attorney, Agent, or Firm* — The Roy Gross Law Firm, LLC; Roy Gross

(57) ABSTRACT

Aspects of embodiments pertain to an intraoperative ophthalmic tissue monitoring system, comprising at least one sensor configured to sense a physical quantity relating to an ophthalmic tissue characteristic of an eye. The system is further configured to provide, responsive to sensing the physical quantity, a sensor output relating to the sensed physical quantity. The system additionally comprises a processor, and a memory comprising for storing software
(Continued)

executable by the processor for enabling the following: controlling, based on the sensor output, a characteristic of ultrasound energy for performing phacoemulsification of a lens of the eye.

20 Claims, 7 Drawing Sheets

(52) U.S. Cl.
CPC ............... *A61B 2017/00115* (2013.01); *A61B 2017/00119* (2013.01)

(58) Field of Classification Search
CPC .............. A61F 9/00745; A61F 9/00736; A61F 9/00763; A61F 9/00754
See application file for complete search history.

(56) References Cited

U.S. PATENT DOCUMENTS

| | | | | |
|---|---|---|---|---|
| 6,083,193 | A * | 7/2000 | Kadziauskas | A61F 9/00745 604/35 |
| 6,699,212 | B1 | 3/2004 | Kadziauskas et al. | |
| 9,050,627 | B2 | 6/2015 | Jacobson | |
| 2011/0295191 | A1* | 12/2011 | Injev | A61M 3/0216 604/65 |
| 2015/0077528 | A1 | 3/2015 | Awdeh | |
| 2015/0148836 | A1 | 5/2015 | Heeren | |
| 2015/0305935 | A1 | 10/2015 | Hajishah et al. | |
| 2016/0346123 | A1 | 12/2016 | Koplin | |
| 2017/0136159 | A1 | 5/2017 | Mallough | |
| 2017/0304018 | A1 | 10/2017 | Papac | |
| 2017/0333253 | A1 | 11/2017 | Heeren et al. | |
| 2018/0078415 | A1 | 3/2018 | Citterio et al. | |
| 2018/0228647 | A1 | 8/2018 | Escaf et al. | |
| 2018/0256392 | A1 | 9/2018 | Wittnebel et al. | |
| 2018/0275429 | A1* | 9/2018 | Pugh | A61B 3/113 |
| 2019/0099547 | A1 | 4/2019 | Mehta et al. | |
| 2019/0133822 | A1 | 5/2019 | Banko | |
| 2020/0107957 | A1* | 4/2020 | Zhang | A61F 9/00745 |

FOREIGN PATENT DOCUMENTS

| | | | |
|---|---|---|---|
| DE | 102015100210 | A1 | 7/2016 |
| DE | 102015100210 | B4 | 7/2020 |

OTHER PUBLICATIONS

Innocenti B., et al., "A Comparison Between Internal and Surface Temperature Measurement Techniques During Phacoemulsification Cataract Surgery: Thermocamera Versus Thermocouple," Journal of Applied Biomaterials & Biomechanics, 2008, vol. 6(3), pp. 151-156.

Jun, B., et al., "Thermal Study of Longitudinal and Torsional Ultrasound Phacoemulsification, Tracking the Temperature of the Corneal Surface, Incision, and Handpiece," Journal of Cataract & Refractive Surgery, May 2010, vol. 36(5), pp. 832-837. DOI: 10.1016/j.jcrs.2009.11.015.

Nair, S., et al., "Wound and Surface Temperatures in Vivo in Torsional and Longitudinal Modalities of Ultrasound in Coaxial Microincisional Cataract Surgery," Clinical Ophthalmology, Jan. 2017, vol. 11, pp. 249-255. DOI: 10.2147/OPTH.S123222.

Ryoo N.K., et al., "Thermal Imaging Comparison of Signature, Infiniti, and Stellaris Phacoemulsification Systems," BMC Ophthalmology, 2013, vol. 13, 53, https://doi.org/10.1186/1471-2415-13-53.

PCT International Search Report and Written Opinion of the International Searching Authority for International Application No. PCT/IB2021/055545, mailed Aug. 19, 2021, 11pp.

Shin S., et al., "Lamellar Keratoplasty using Position-Guided Surgical Needle and M-Mode Optical Coherence Tomography," Journal of Biomedical Optics, Dec 2017, vol. 22(12), 125005, 8 pages, doi: 10.1117/1.JBO.22.12.125005.

* cited by examiner

INTRAOPERATIVE OPHTHALMIC TISSUE MONITORING DEVICE, SYSTEM AND METHOD

CROSS-REFERENCE TO RELATED APPLICATIONS

This application is a National Phase of PCT Patent Application No. PCT/IB2021/055545 having International filing date of Jun. 23, 2021, which claims priority from U.S. Provisional Patent Application 63/042,840 filed on Jun. 23, 2020, the contents of which are all expressly incorporated herein by reference in their entirety.

BACKGROUND

Cataract surgery is a procedure employed for removing a patient's cloudy lens to replace it with an intraocular lens (IOL) lens implant.

Modern cataract extraction is done using phacoemulsification device which utilizes ultrasound energy to disassemble the cataract. The energy is produced by the device's tip and located in the anterior chamber of the eye to perform phacoemulsification.

Cataract surgery includes the procedure of employing a phacoemulsification (also: "Phaco") device for subjecting the eye's lens with ultrasound (US) energy to disintegrate the lens into lens fragments which are aspirated from the patient's eye.

The amount of energy applied for disintegrating the lens is controlled by the surgeon.

BRIEF DESCRIPTION OF THE FIGURES

The subject matter regarded as the invention is particularly pointed out and distinctly claimed in the concluding portion of the specification. The invention is best understood in view of the accompanying drawings in which:

Figure 1:
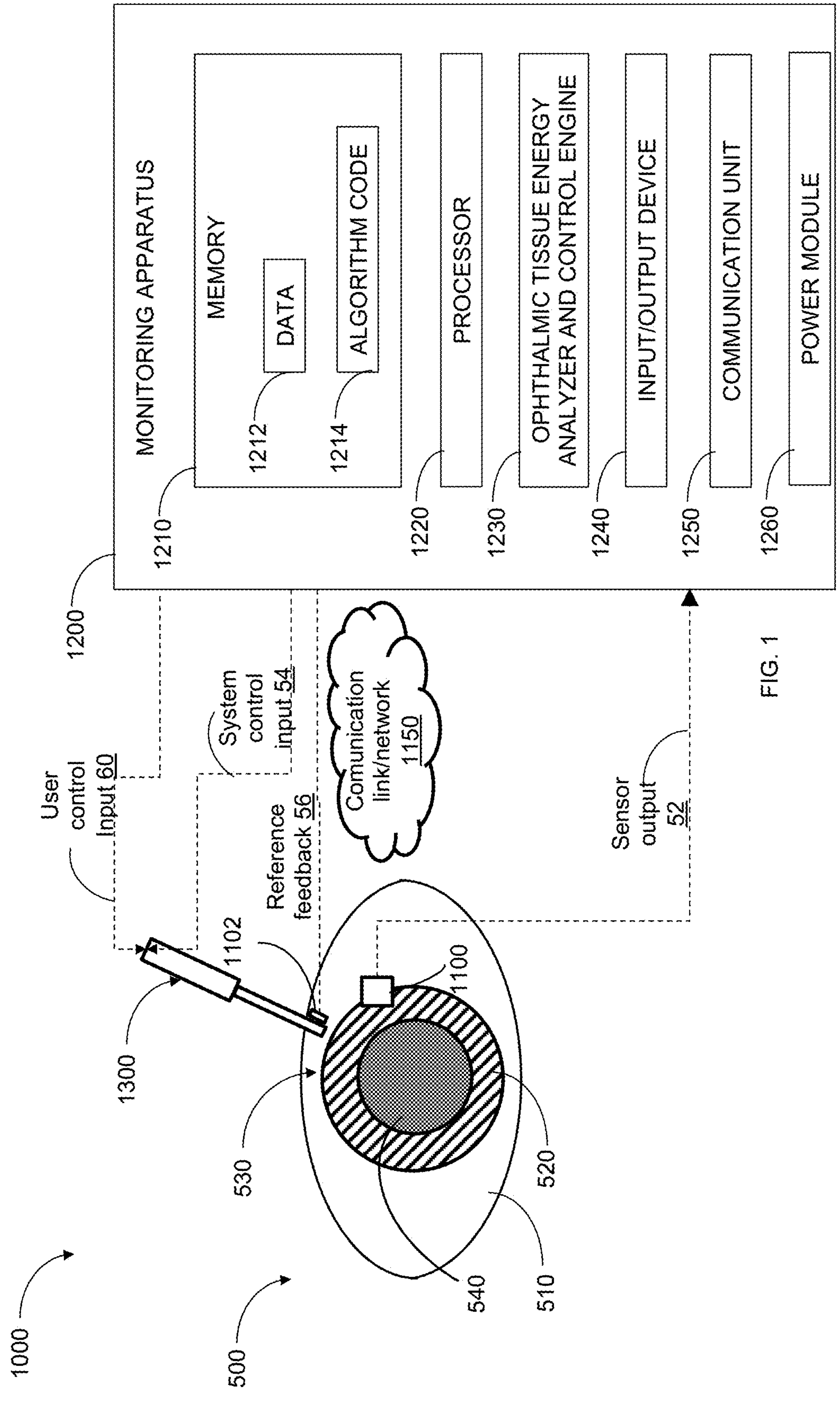
FIG. 1 is a schematic illustration of an ophthalmic tissue monitoring system, according to an embodiment.

It will be appreciated that for the sake of clarity, elements shown in the figures may not be drawn to scale and reference numerals may be repeated in different figures to indicate corresponding or analogous elements.

DETAILED DESCRIPTION

The following description, certain details are set forth to facilitate understanding; however, it should be understood by those skilled in the art that the present invention may be practiced without these specific details. Furthermore, well-known methods, procedures, and components have not been omitted to highlight the invention.

Applying US energy too excessively for the purpose of lens fragmentation may lead to collateral or unwanted tissue damage including, for example, corneal endothelial damage which, in turn, can cause corneal edema including pain and loss of vision. Corneal edema, also known as Pseudophakic bullous keratopathy (PBK), may in some cases require corneal transplantation.

Aspects of embodiments pertain to an intraoperative ophthalmic tissue monitoring system which is configured to prevent damage to ophthalmic tissue due to the application of US energy to the eye's lens in phacoemulsification procedures.

The sensor output may be processed for displaying information to the user and/or for (e.g., performing the automatic or facilitating the semi-automatic) controlling of the characteristic of the ultrasound to be applied to the ophthalmic tissue.

In some examples, the processing comprises determining whether the sensor output meets one or more alert criteria for displaying, for example, an alert for the prevention of damage of ophthalmic tissue such as the cornea because of applying ultrasound energy. In some further examples, guidance may be provided to the medical professional regarding the amount and/or timing of ultrasound energy application to the eye lens without causing damage ophthalmic tissue. In some examples, the processing comprises modulating a value of a characteristic of the ultrasound energy to be applied for performing phacoemulsification in a manner that prevents damage to ophthalmic tissue (e.g., cornea). The modulation is performed during application of the ultrasound energy to the ophthalmic tissue.

An alert criterion may for example be met if a sensor output exceeds a threshold value in relation to a sensed physical quantity. For example, if the sensor output exceeds a certain magnitude in relation to sensed temperature, noise, strain and/or sensed auditory level, the alert criterion may be met. For example, above a sensed amplitude of 0.05 at a frequency 2 kHz, during a time period of 2 sec, the applied amplitude is automatically reduced by 30%.

The sensor may provide the sensor output in real-time or near real-time. Accordingly, the automatic controlling of the ultrasound transducer is performed in real-time or in near real-time to prevent damage of ophthalmic tissue such as, for example, damage of the cornea (e.g., corneal endothelial damage or Pseudophakic bullous keratopathy).

Referring now to FIG. 1, a front view of an eye 500 with its sclera 510, iris 520, cornea 530 and (expanded) pupil 540 are shown along with a sensor 1100 that is in operable communication with a sensor 1100 of an ophthalmic tissue monitoring system 1000. In some examples, sensor 1100 may engage with ophthalmic tissue. In some other examples, sensor 1100 may be physically disengaged from ophthalmic tissue.

Sensor 1100 is configured to sense a physical quantity relating to at least one ophthalmic tissue characteristic of an eye and to provide a sensor output 52 relating to the sensed physical quantity. Sensor output 52 may be provided by sensor 1100 responsive to the sensing of the physical quantity.

Sensor output 52 may, for example, relate to one of the following physical quantities: ophthalmic tissue temperature, tissue color, normal strain, shear strain; normal pressure, shear stress, vibrations to which the ophthalmic tissue may be subjected to, or any combination of the aforesaid.

The at least one sensor 1100 may employ one of the following sensing modalities: fiber-optical sensing; thermal sensing; conductivity measurement sensing; MEMS-based vibration sensing; remote sensing, tissue-engaging sensor, or any combination of the aforesaid. Optionally, part of sensor 1100 or all of sensor 1100 may be disposable.

For example, a microphone sensor may be employed to derive from the sound waves sensed by the microphone sensor 1100 and converted into corresponding sound data, an operational scenario and/or a physical quantity relating to at least one ophthalmic tissue characteristic. For example, as will be outlined herein below in more detail, such microphone sensor may be employed to identify if one of the following situations:

A) the phacoemulsification tip engages with the cornea;
B) the phacoemulsification tip is close to the cornea but does not touch it; or
C) the phacoemulsification tip is comparatively far away from the cornea (i.e., further away than in B). For example, the distance between the phacoemulsification tip and the cornea is at least 0.5 cm.

In some embodiments, based on the sensor output 52, a characteristic of ultrasound energy to be applied to the ophthalmic tissue for performing phacoemulsification by phacoemulsification device 1300 having an output tip, can be controlled.

In some embodiments, phacoemulsification device 1300 may be considered part of system 1000. In some other embodiments, phacoemulsification device 1300 may not be considered part of system 1000.

In some embodiments, sensor 1100 is external to or physically decoupled from phacoemulsification device 1300 such that the sensor's sensing capabilities are independent of the position of a phacoemulsification device 1300 relative to ophthalmic tissue, e.g., as outlined herein below. In some embodiments, a position of the sensor relative to the ophthalmic tissue is independent of a position of a phacoemulsification device employed for applying the ultrasound. In some embodiments, a relative position of the sensor with respect to the ophthalmic tissue is constant.

In some embodiments, a reference sensor 1102 may be employed, e.g., in addition to sensor 1100. Reference sensor 1102 may be employed by or be part of phacoemulsification device 1300 and configured to sense an ultrasound characteristic that is output by the tip of phacoemulsification device 1300 and further configured to provide monitoring apparatus 1200 with a corresponding reference output 56. Reference sensor 1102 may be employed to detect and, optionally, correct for discrepancies between an operator or user control input 60 provided by the user (e.g., a medical professional such as a physician, ophthalmologist, eye surgeon), for example, via the system's foot pedal(s) (not shown) and the actual ultrasound power output as sensed by reference sensor 1102. In some embodiments, the reference output 56 provided by reference sensor 1102 may be used to (e.g., automatically) calibrate the user's output, e.g., on-the-fly, while performing phacoemulsification.

A characteristic of ultrasound may include, for example, one of the following: duration for operably applying ultrasound to the ophthalmic lens, a frequency, a phase, a phase difference, an amplitude, power, or any combination of the aforesaid.

As schematically shown in FIG. 1, sensor output 52 may be provided by sensor 1100 to a monitoring apparatus 1200.

Monitoring apparatus 1200 may be implemented by a computerized end-user device may include a multifunction mobile communication device also known as "smartphone", a personal computer, a laptop computer, a tablet computer, a server (which may relate to one or more servers or storage systems and/or services associated with a business or corporate entity, including for example, a file hosting service, cloud storage service, online file storage provider, peer-to-peer file storage or hosting service and/or a cyberlocker), personal digital assistant, a workstation, a wearable device, a handheld computer, a notebook computer.

Monitoring apparatus 1200 may comprise a memory 1210 and a processor 1220. Memory 1210 may comprise data 1212 and algorithm code (e.g., a rule engine and/or a machine learning model such as) 1214 executable by processor 1220 to result in an ophthalmic tissue analyzer and control (OTAC) engine 1230.

Memory 1210 may include one or more types of computer-readable storage media such as transactional memory and/or long-term storage memory facilities and may function as file storage, document storage, program storage, or as a working memory. The latter may for example be in the form of a static random access memory (SRAM), dynamic random access memory (DRAM), read-only memory (ROM), cache and/or flash memory. As working memory, memory 1210 may, for example, including, e.g., temporally-based and/or non-temporally based instructions. As long-term memory, memory 1210 may for example include a volatile or non-volatile computer storage medium, a hard disk drive, a solid state drive, a magnetic storage medium, a flash memory and/or other storage facility. A hardware memory facility may for example store a fixed information set (e.g., software code) including, but not limited to, a file, program, application, source code, object code, data, and/or the like.

The term "processor", as used herein, may additionally or alternatively refer to a controller. Processor 1220 may be implemented by various types of processor devices and/or processor architectures including, for example, embedded processors, communication processors, graphics processing unit (GPU)-accelerated computing, soft-core processors and/or general purpose processors. It will be appreciated that separate processors can be allocated for each element or processing function in system 1000. For simplicity, the following description will refer to processor 1220 as a generic processor which conducts all the necessary processing functions of system 1000.

In some embodiments, OTAC engine 1230 may cause, via an input/output device 1240, provide information relating to sensor output 52. Based on the output information, a medical professional may, for example, adjust, adapt or control a phacoemulsification operating parameter value applied to the lens by phacoemulsification device 1300 for performing phacoemulsification.

Although embodiments and examples may herein be disclosed with respect to preventing or decreasing the chance of inflicting damage to the cornea, this should by no means be construed in a limiting manner. Accordingly, the systems and method disclosed herein may also be applicable to prevent inflicting damage to other ophthalmic tissue during phacoemulsification.

Input/output device 1240 may include, for example, visual presentation devices or systems such as, for example, computer screen(s), head mounted display (HMD) device (s), first person view (FPV) display device(s), device interfaces (e.g., a Universal Serial Bus interface), and/or audio output device(s) such as, for example, speaker(s) and/or earphones. Input/output device 1240 may be employed to access information generated by the system and/or to provide inputs including, for instance, control commands, operating parameters, queries and/or the like.

For example, input/output device 1240 may allow a user of monitoring system 1000 to perform one or more of the following: approval of system-suggested treatment protocol and/or of their attributes; control of ultrasound treatment parameter values. In some embodiments, monitoring apparatus 1200 may be configured to provide treatment recommendations.

In some embodiments, information that may be output by OTAC engine 1230 may be indicative of one or more of the following: an alert that the subject's or mammalian's cornea may become damaged; an alert that excessive ultrasound power is applied to the subject's cornea; an output indicating that the tip of phacoemulsification device 1300 is too close to the subject's cornea; an output that the tip of phacoemulsification device 1300 is engaging with the subject's cornea; an output indicating that the cornea is subjected to increased ultrasound energy or power; an output indicating that the cornea is subjected to decreasing ultrasound energy or power; an output indicating that the lens is subjected to insufficient amount of ultrasound energy or power; an output relating to a treatment recommendation including, for example, a recommended amount of ultrasound power increase or decrease; a recommended relative positioning of the tip of phacoemulsification device 1300 relative to the lens and the cornea; and/or the like.

In some embodiments, based on the sensor output 52, OTAC engine 1230 may automatically control or allow semi-automatic control one or more ultrasound energy characteristics which are to be applied to the ophthalmic lens for performing phacoemulsification. This may be accomplished by providing, based on sensor output 52, a system control feedback or input 54 from the monitoring apparatus 1200 to phacoemulsification device 1300.

For example, in case an alert criterion is met, monitoring apparatus 1200 may provide system control input 54 to decrease the magnitude of ultrasound power output by phacoemulsification device 1300 to drop below a safe threshold. In some examples, in case an alert criterion is met, system control input 54 provided by monitoring apparatus 1200 may cause shut down of phacoemulsification device 1300. In some examples, system control input 54 that is provided by monitoring apparatus 1200 in case an alert criterion is met, overrides or takes precedence over a user control input 60 that may be provided by the user (e.g., via a foot pedal) of monitoring system 1000 (e.g., ophthalmologist) for performing phacoemulsification of the subject's lens.

In some embodiments, OTAC engine 1230 may have or employ artificial intelligence functionalities which are based on Machine learning models such as, for example, support vector machine, knn, kmeans, and artificial (e.g., convolutional) neural network, etc., to determine, based on sensor output 52, an phacoemulsification output intensity, frequency, and/or tip location which reduces or minimizes the risk of inadvertently inflicting damage to ophthalmic tissue (e.g., cornea), while increasing or maximizing the speed of the phacoemulsification procedure.

Monitoring Apparatus 1200 may comprise a communication module 1250 for facilitating wired and/or wireless communication with sensor 1100 over a communication link or communication network 1150, for example, for providing sensor output 52 from sensor 1100 to monitoring apparatus 1200 and for providing control feedback 54 from monitoring apparatus 1200 to phacoemulsification device 1300.

Communication module 1250 may, for example, include I/O device drivers (not shown) and network interface drivers (not shown) for enabling the transmission and/or reception of data over network link or network 1150. A device driver may for example, interface with a keypad or to a USB port. A network interface driver may for example execute protocols for the Internet, or an Intranet, Wide Area Network (WAN), Local Area Network (LAN) employing, e.g., Wireless Local Area Network (WLAN)), Metropolitan Area Network (MAN), Personal Area Network (PAN), extranet, 2G, 3G, 3.5G, 4G including for example Mobile WIMAX or Long Term Evolution (LTE) advanced, Bluetooth® (e.g., Bluetooth smart), ZigBee™, near-field communication (NFC) and/or any other current or future communication network, standard, and/or system.

Monitoring apparatus 1200 may further include a power module 1260 for powering the various components, applications and/or elements of monitoring apparatus 1200 and/or sensor 1100.

The various components of monitoring apparatus 1200 may communicate with each other over one or more communication buses (not shown) and/or signal lines (not shown).

Power module 1260 may comprise an internal power supply (e.g., a rechargeable battery) and/or an interface for allowing connection to an external power supply.

Figure 2A:
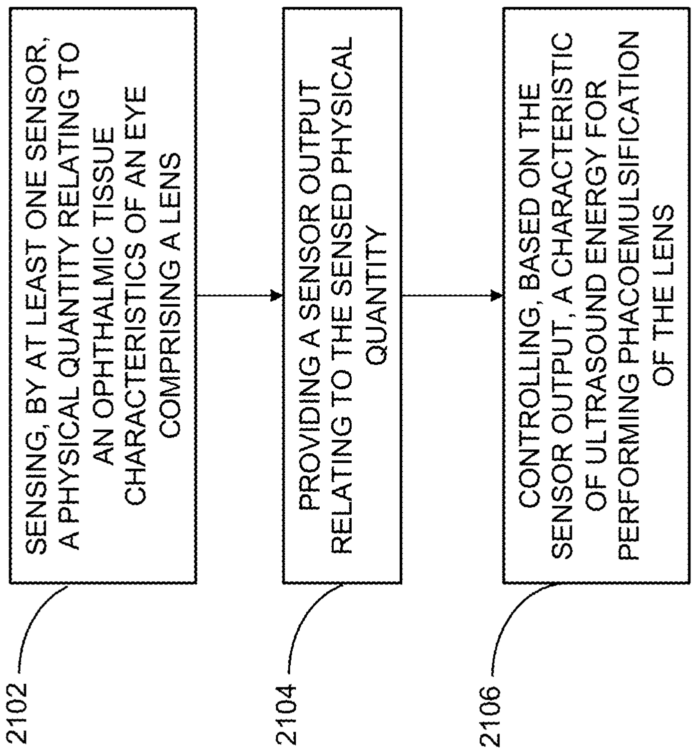
FIG. 2A is a schematic flow chart of a method for performing intraoperative ophthalmic tissue monitoring, according to an embodiment.

Further reference is made to FIG. 2A. According to some embodiments, a method for intraoperatively monitoring ophthalmic tissue may include, for example, sensing, by at least one sensor 1100, a physical quantity relating to an ophthalmic tissue characteristic of eye 500 (block 2102).

In some embodiments, the method may further include, for example, providing a sensor output relating to the sensed physical quantity (block 2104). The sensor output may be provided by sensor 1100 responsive to the sensing of the physical quantity.

In some embodiments, the method may include controlling, based on the sensor output, a characteristic of ultrasound power to be applied for performing phacoemulsification of a lens of the eye (block 2106).

Figure 2B:
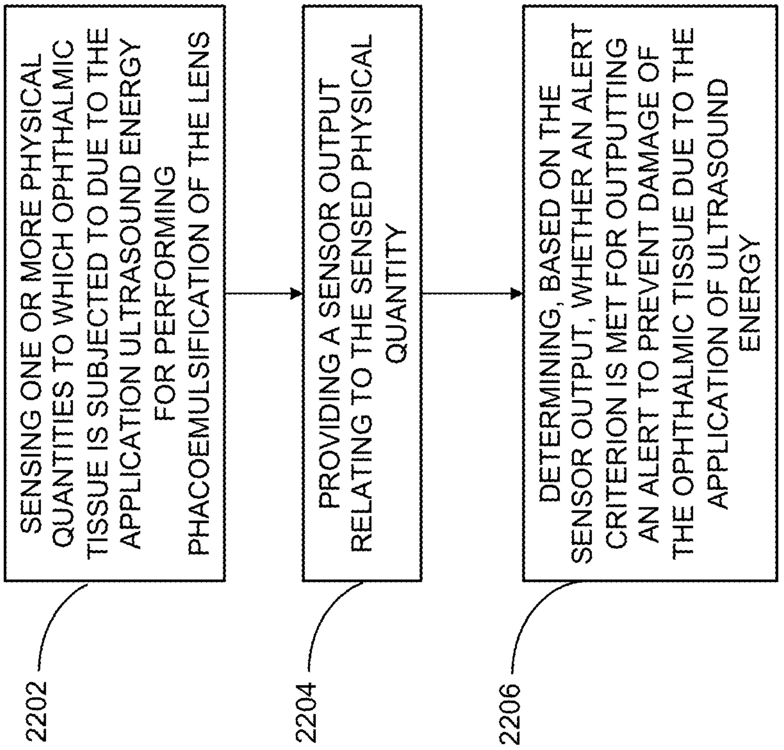
FIG. 2B is a schematic flow chart of a method for performing intraoperative ophthalmic tissue monitoring, according to a further embodiment.

Further reference is made to FIG. 2B. According to some embodiments, a method for intraoperatively monitoring ophthalmic tissue may include, for example, sensing one or more physical quantities to which ophthalmic tissue is subjected to due to the application of ultrasound for performing phacoemulsification of the lens. (block 2202).

In some embodiments, the method may further include, for example, providing a sensor output relating to the sensed physical quantity (block 2204). The sensor output may be provided by sensor 1100 responsive to the sensing of the physical quantity.

In some embodiments, the method may include determining, based on the sensor output, whether an alert criterion is met for outputting an alert to prevent damage of the ophthalmic tissue due to the application of ultrasound (block 2206). In some embodiments, after the step of block 2206, the step of block 2106 may be performed.

First Experiment

Figure 3A:
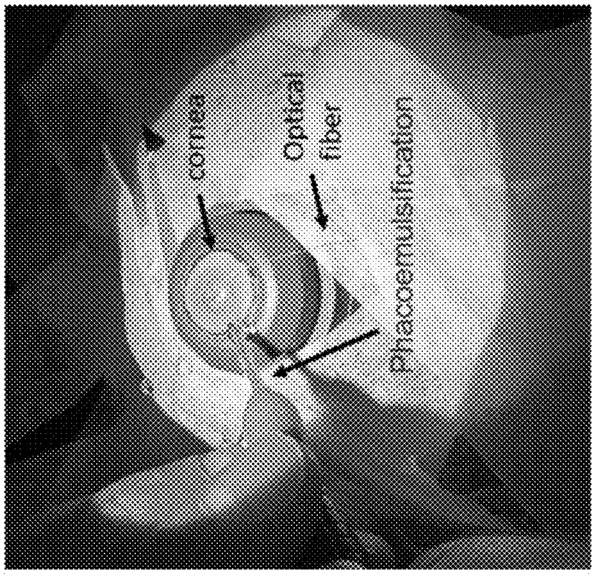
FIG. 3A is an image of a setup for conducting a first experiment for measuring vibrating strains of a corneal endothelium.
Figure 3B:
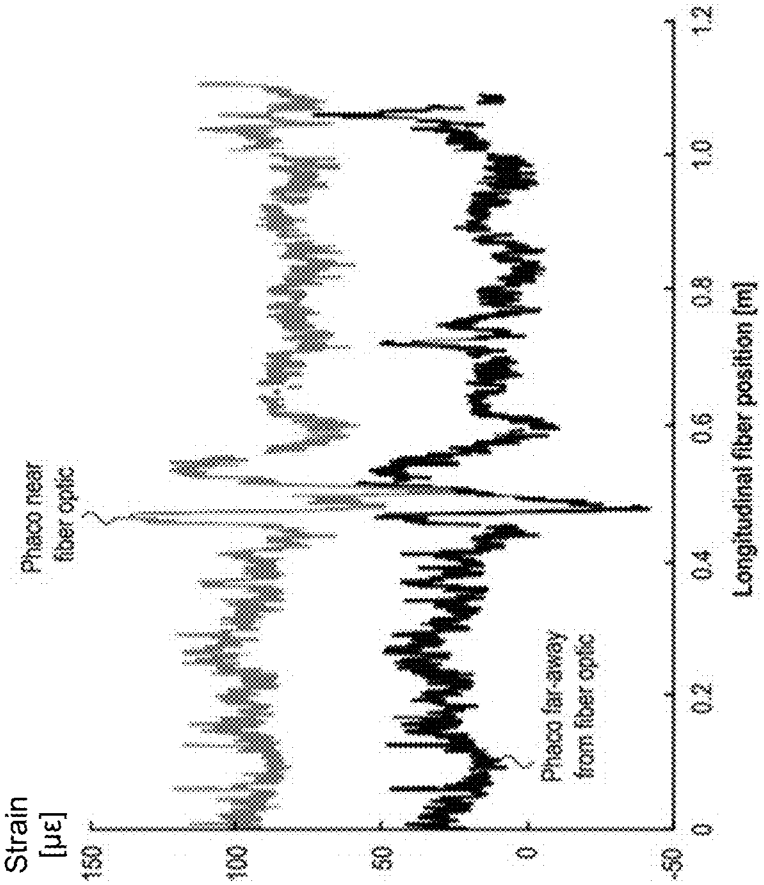
FIG. 3B shows the measured vibrating strain, depending on the proximity of a phacoemulsification device relative to the corneal endothelium.

Additional reference is made to FIGS. 3A and B. In a first experiment, a Rayleigh-scattering-based optic fiber strain and temperature sensor were attached, using transparent lacquer onto the cornea surface using an artificial anterior chamber (FIG. 3A). Phacoemulsification was employed inside the anterior chamber. The measured signals (FIG. 3B) show variable degrees of vibrating strain, depending on the proximity of the phacoemulsification device relative the corneal endothelium. The upper gray graph represents strain measured at the mock cornea with a fiber optic-based sensor when the phaco tip is comparatively near the mock cornea, and the black graph represents strain measured at the mock cornea with the fiber optic-based sensor when the phaco tip is positioned further away from the mock cornea. As shown, the strain measured when the phaco-tip was closer to the mock cornea is greater in magnitude than the measured strain when the phaco-tip was positioned further away from the mock cornea.

Second Experiment

Figure 4A:
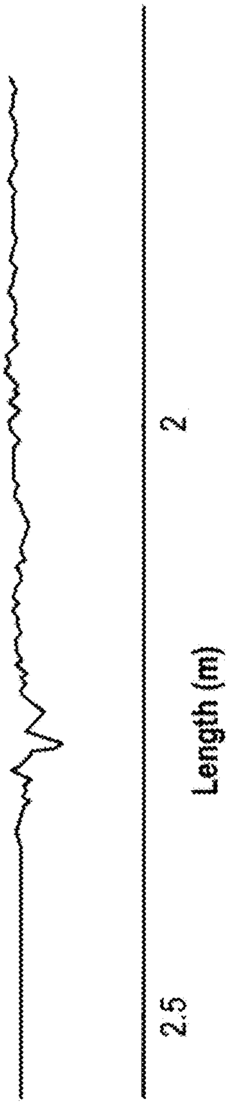
FIG. 4A shows the temperature along the same optical fiber which was used for conducting the experiments outlined with respect to FIGS. 3A and 3B, when the mock cornea was not subjected to ultrasound energy.
Figure 4B:
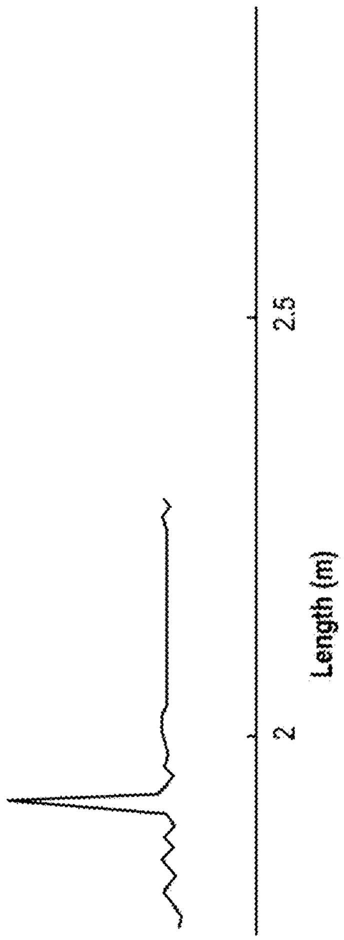
FIG. 4B shows an increase in measured temperature at the position where the optical fiber engaged with the mock cornea when it was subjected to ultrasound energy.

Referring to FIGS. 4A and 4B, the same sensor as in the first example was employed to measure with the optical fiber the temperature of the corneal endothelium, with FIG. 4A showing the measured temperature (in degrees Celsius) along the optical fiber when the mock cornea was not subjected to ultrasound for phacoemulsification. FIG. 4B shows the increase in measured temperature of the corneal endothelium at a position where the optical fiber engaged with the mock cornea.

Third Experiment

Figure 5:
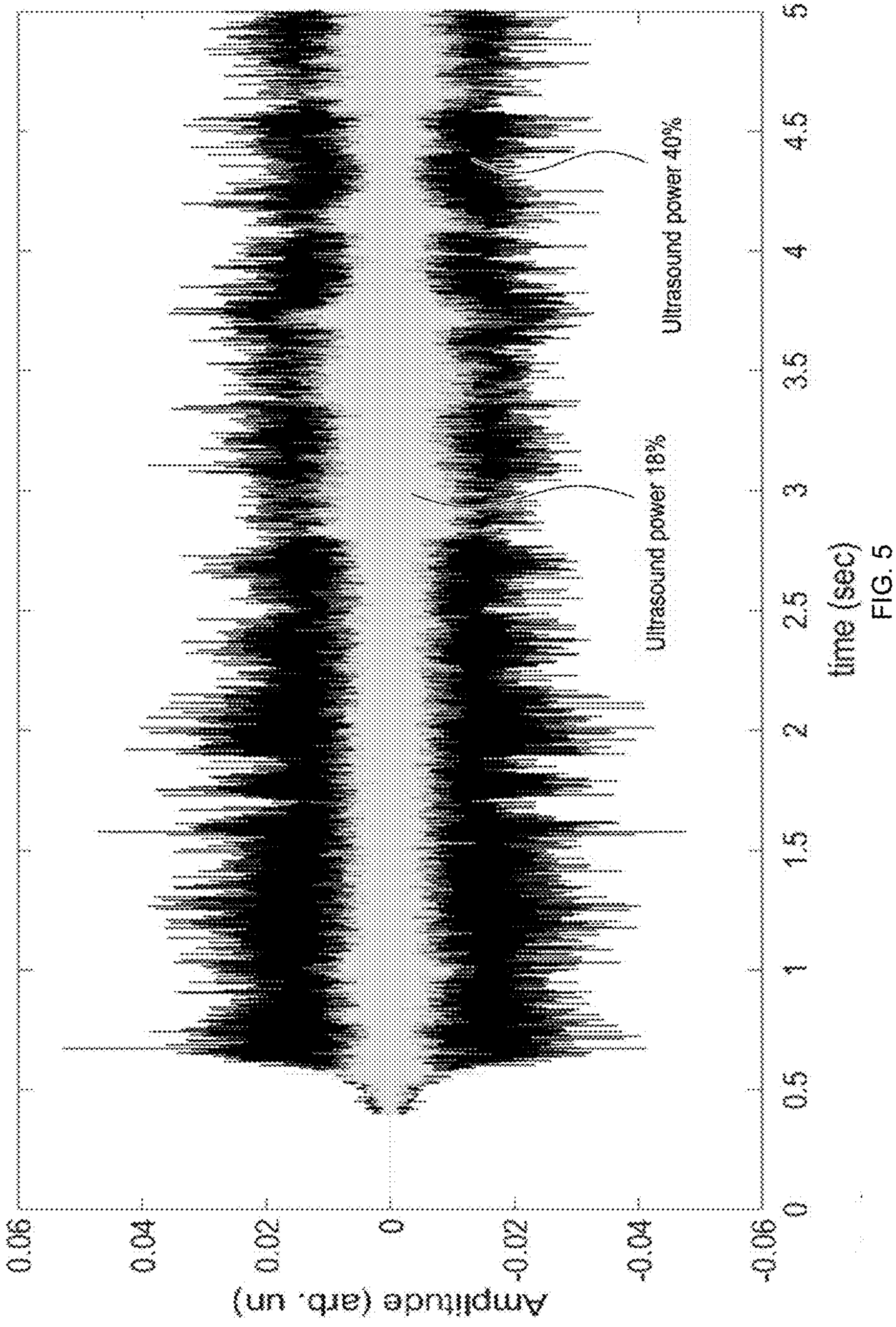
FIG. 5 shows audio signals which were output by a microphone sensor that was attached to an external plastic artificial cornea surface of an eye model, in response to applying ultrasound at different power levels to a plastic artificial cornea surface applied in the artificial anterior chamber of the eye model.
Figure 6A:
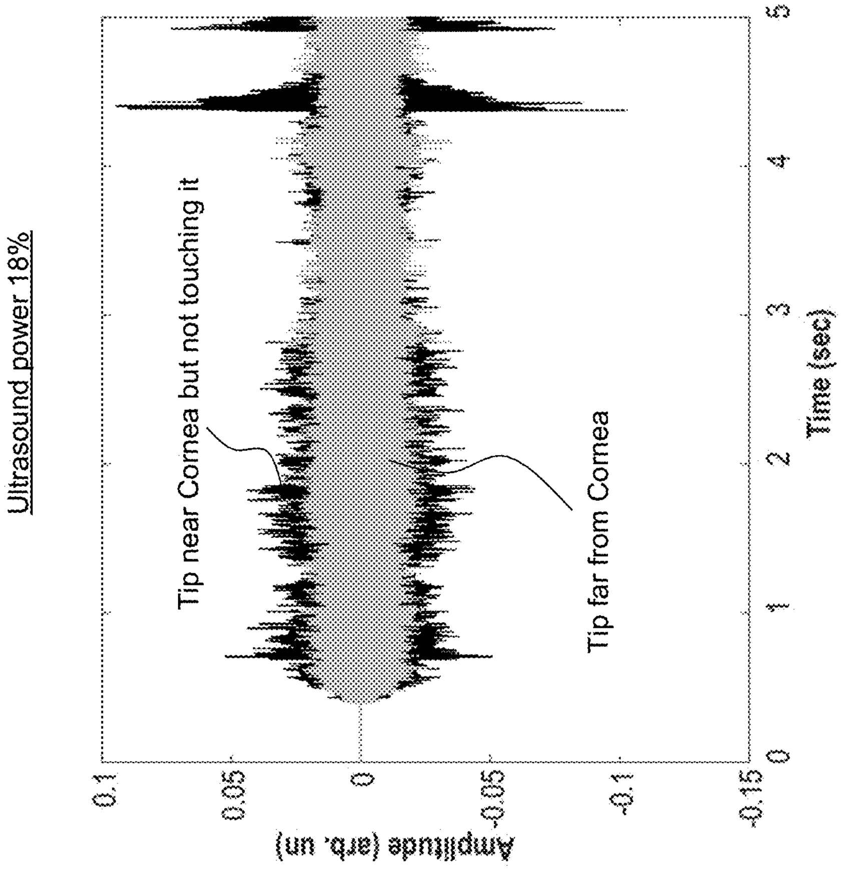
FIG. 6A shows, for a selected ultrasound power level, the audio signals of sensed sound picked up during a mock phacoemulsification procedure applied on the eye model, where the phacoemulsification tip was comparatively far from the artificial cornea and for a scenario where the tip was near but not touching the artificial cornea.

FIG. 5 shows in the time domain audio signals which were output by a microphone sensor that was attached to an external plastic artificial cornea surface of an eye model, in response to applying phacoemulsification power at different power levels to a plastic artificial cornea surface (or mock cornea) that was applied in the mock artificial anterior chamber of the eye model. The gray area represents that measured signals for ultrasound power applied at 18%. The black areas represents that measured signals for ultrasound power applied at 40%;

FIG. 6A shows, for a selected ultrasound power level of 18%, the audio signals of sensed sound picked up during a mock phacoemulsification procedure applied on the eye model, where the phacoemulsification tip was comparatively far from the artificial or mock cornea (gray area of audio signal) and for a scenario where the tip was near but not touching the artificial cornea (black area of audio signal).

Figure 6B:
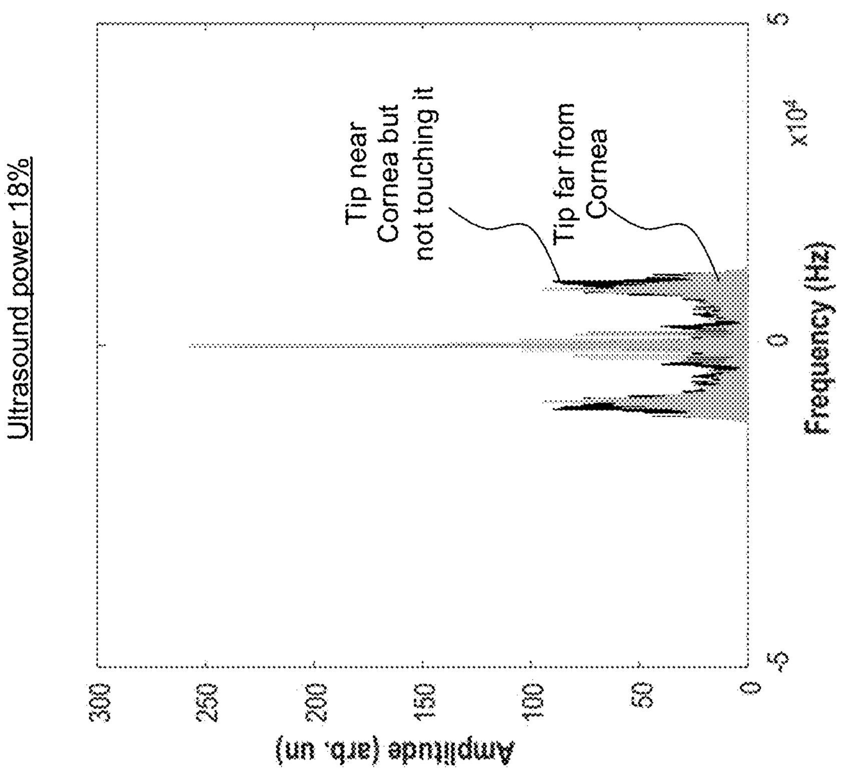
FIG. 6B shows the frequency components of the signal shown in FIG. 6A.

FIG. 6B shows the frequency components of the signal shown in FIG. 6A. As can readily be seen, the measured sound amplitude increased the closer the tip was positioned relative to the mock cornea.

Figure 7B:
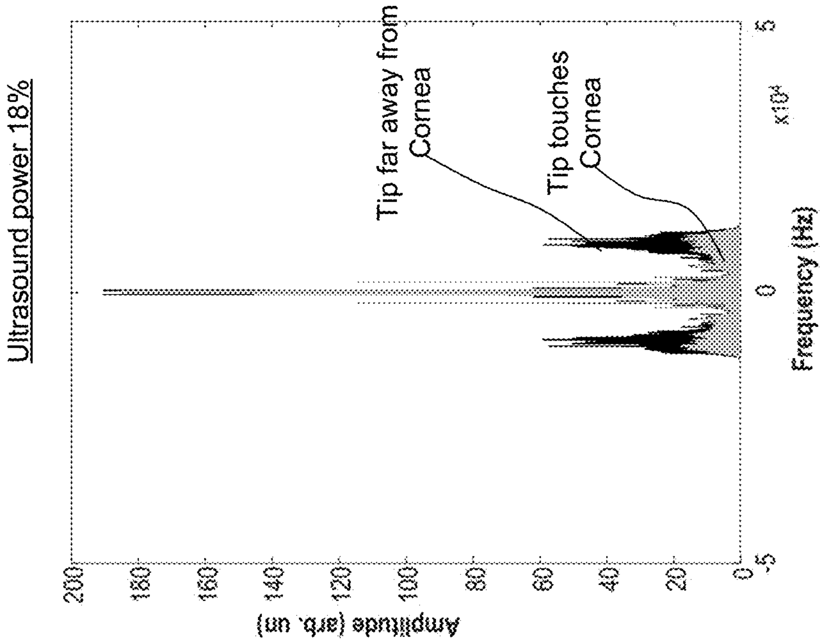
FIG. 7B shows in the frequency domain the signals illustrated in FIG. 7A.
Figure 7A:
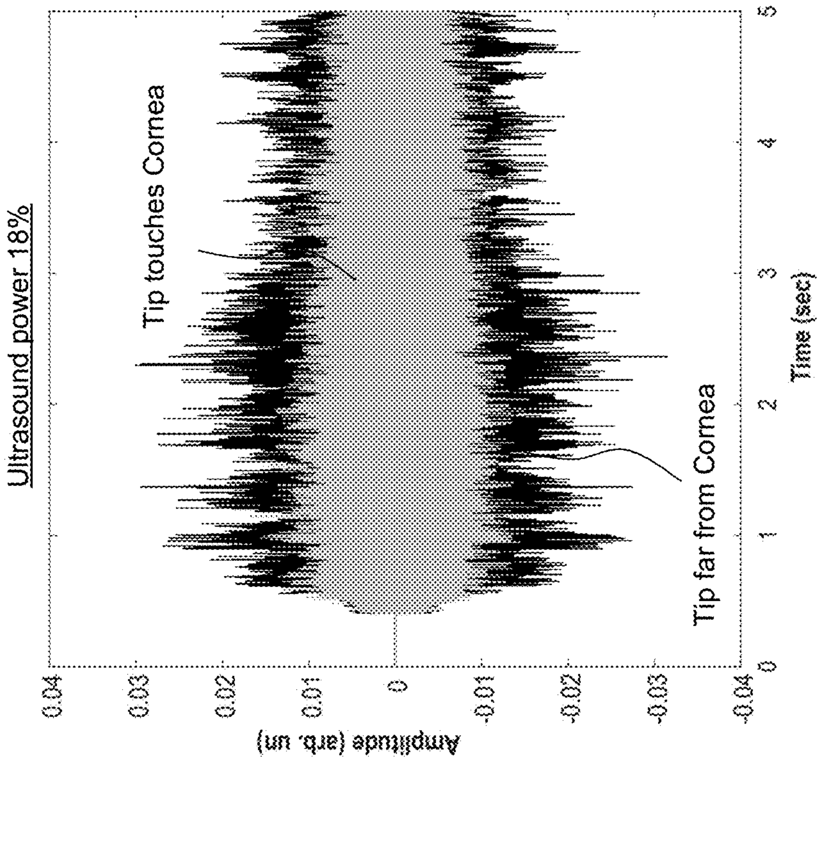
FIG. 7A shows, for a selected ultrasound power level applied in another mock phacoemulsification procedure applied on the eye model, in the time domain, the audio signals of sensed sound for a scenario where the phacoemulsification tip was comparatively far from the artificial cornea and for a scenario where the tip was touching the artificial cornea.

FIG. 7A shows, for a selected ultrasound power level of 18% applied in another mock phacoemulsification procedure applied on the eye model, in the time domain, the audio signals of sensed sound for a scenario where the phacoemulsification tip was comparatively far from the artificial cornea (black area) and for a scenario where the tip touched the artificial cornea (gray area). When the tip touched the mock cornea, the sensed sound amplitudes decreased. However, in a real-life setting, this would of course destroy the cornea.

FIG. 7B shows in the frequency domain the signals illustrated in FIG. 7A.

All the experiments demonstrated that it is feasible to determine an alert criterion based on sensor output for displaying various alert and/or for providing corresponding (e.g., overriding) control outputs, to reduce the risk or prevent damage of a mammalian's corneal endothelium, for example.

It is important to note that the methods described herein and illustrated in the accompanying diagrams shall not be construed in a limiting manner. For example, methods described herein may include additional or even fewer processes or operations in comparison to what is described herein and/or illustrated in the diagrams. In addition, method steps are not necessarily limited to the chronological order as illustrated and described herein.

Any digital computer system, unit, device, module and/or engine exemplified herein can be configured or otherwise programmed to implement a method disclosed herein, and to the extent that the system, module and/or engine is configured to implement such a method, it is within the scope and spirit of the disclosure. Once the system, module and/or engine are programmed to perform particular functions pursuant to computer readable and executable instructions from program software that implements a method disclosed herein, it in effect becomes a special purpose computer particular to embodiments of the method disclosed herein. The methods and/or processes disclosed herein may be implemented as a computer program product that may be tangibly embodied in an information carrier including, for example, in a non-transitory tangible computer-readable and/or non-transitory tangible machine-readable storage device. The computer program product may directly loadable into an internal memory of a digital computer, comprising software code portions for performing the methods and/or processes as disclosed herein.

The methods and/or processes disclosed herein may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by one or more communication networks.

These computer readable and executable instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable and executable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable and executable instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The term "engine" may comprise one or more computer modules, wherein a module may be a self-contained hardware and/or software component that interfaces with a larger system. A module may comprise a machine or machines executable instructions. A module may be embodied by a circuit, or a controller programmed to cause the system to implement the method, process and/or operation as disclosed herein. For example, a module may be implemented as a hardware circuit comprising, e.g., custom VLSI circuits or gate arrays, an Application-Specific Integrated Circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Unless otherwise specified, the terms "substantially", "about" and/or "close" with respect to a magnitude or a numerical value may imply to be within an inclusive range of −10% to +10% of the respective magnitude or value.

"Coupled with" can mean indirectly or directly "coupled with".

It is important to note that the method may include is not limited to those diagrams or to the corresponding descriptions. For example, the method may include additional or even fewer processes or operations in comparison to what is described in the figures. In addition, embodiments of the method are not necessarily limited to the chronological order as illustrated and described herein.

Discussions herein utilizing terms such as, for example, "processing", "computing", "calculating", "determining", "establishing", "analyzing", "checking", "estimating", "deriving", "selecting", "inferring" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes. The term determining may, where applicable, also refer to "heuristically determining".

It should be noted that where an embodiment refers to a condition of "above a threshold", this should not be construed as excluding an embodiment referring to a condition of "equal or above a threshold". Analogously, where an embodiment refers to a condition "below a threshold", this should not be construed as excluding an embodiment referring to a condition "equal or below a threshold". It is clear that should a condition be interpreted as being fulfilled if the value of a given parameter is above a threshold, then the same condition is considered as not being fulfilled if the value of the given parameter is equal or below the given threshold. Conversely, should a condition be interpreted as being fulfilled if the value of a given parameter is equal or above a threshold, then the same condition is considered as not being fulfilled if the value of the given parameter is below (and only below) the given threshold.

It should be understood that where the claims or specification refer to "a" or "an" element and/or feature, such reference is not to be construed as there being only one of that element. Hence, reference to "an element" or "at least one element" for instance may also encompass "one or more elements".

Terms used in the singular shall also include the plural, except where expressly otherwise stated or where the context otherwise requires.

In the description and claims of the present application, each of the verbs, "comprise" "include" and "have", and conjugates thereof, are used to indicate that the data portion or data portions of the verb are not necessarily a complete listing of components, elements or parts of the subject or subjects of the verb.

Unless otherwise stated, the use of the expression "and/or" between the last two members of a list of options for selection indicates that a selection of one or more of the listed options is appropriate and may be made. Further, the use of the expression "and/or" may be used interchangeably with the expressions "at least one of the following", "any one of the following" or "one or more of the following", followed by a listing of the various options.

As used herein, the phrase "A,B,C, or any combination of the aforesaid" should be interpreted as meaning all of the following: (i) A or B or C or any combination of A, B, and C, (ii) at least one of A, B, and C; (iii) A, and/or B and/or C, and (iv) A, B and/or C. Where appropriate, the phrase A, B and/or C can be interpreted as meaning A, B or C. The phrase A, B or C should be interpreted as meaning "selected from the group consisting of A, B and C". This concept is illustrated for three elements (i.e., A,B,C), but extends to fewer and greater numbers of elements (e.g., A, B, C, D, etc.).

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, examples and/or optional implementation are not to be considered essential features of those embodiments, unless the embodiment, example and/or optional implementation is inoperative without those elements.

It is noted that the terms "in some embodiments", "according to some embodiments", "for example", "e.g.", "for instance" and "optionally" may herein be used interchangeably.

The number of elements shown in the Figures should by no means be construed as limiting and is for illustrative purposes only.

"Real-time" as used herein generally refers to the updating of information at essentially the same rate as the data is received. More specifically, in the context of the present invention "real-time" is intended to mean that the image data is acquired, processed, and transmitted from a sensor at a high enough data rate and at a low enough time delay that when the data is displayed, data portions presented and/or displayed in the visualization move smoothly without user-noticeable judder, latency or lag.

It is noted that the terms "operable to" can encompass the meaning of the term "modified or configured to". In other words, a machine "operable to" perform a task can in some embodiments, embrace a mere capability (e.g., "modified") to perform the function and, in some other embodiments, a machine that is actually made (e.g., "configured") to perform the function.

Throughout this application, various embodiments may be presented in and/or relate to a range format. It should be understood that the description in range format is merely for convenience and brevity and should not be construed as an inflexible limitation on the scope of the embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

While the invention has been described with respect to a limited number of embodiments, these should not be construed as limitations on the scope of the invention, but rather as exemplifications of some of the embodiments.

ADDITIONAL EXAMPLES

Example 1 pertains to an intraoperative ophthalmic tissue monitoring system, comprising: at least one sensor configured to sense a physical quantity relating to an ophthalmic tissue characteristic of an eye, providing, responsive to sensing the physical quantity, a sensor output relating to the sensed physical quantity, a processor, and a memory comprising for storing software executable by the processor for enabling the following: controlling, based on the sensor output, a characteristic of ultrasound energy for performing phacoemulsification of a lens of the eye.

Example 2 includes the subject matter of Example 1 and, optionally, displaying information related to the sensor output for facilitating the controlling of a characteristic value of ultrasound energy by a medical professional.

Example 3 includes the subject matter of Examples 1 and/or 2 and, optionally, performing the controlling automatically based on the received sensor output by providing a control feedback to a phacoemulsification device.

Example 4 includes the subject matter of any one or more of the examples 1 to 3 and, optionally, wherein the sensor output is processed for performing the displaying to the medical professional and/or for performing the automatic controlling of the characteristic of the ultrasound energy to be applied to the ophthalmic tissue.

Example 5 includes the subject matter of any one or more of the examples 1 to 4 and, optionally, wherein the processing comprises determining whether the sensor output meets one or more criteria for displaying an alert.

Example 6 includes the subject matter of any one or more of the examples 1 to 5 and, optionally, wherein the processing comprises determining whether the sensor output meets one or more criteria for modulating a value of a characteristic of the ultrasound energy.

Example 7 includes the subject matter of any one or more of the examples 5 and/or 6, wherein the one or more criteria pertain to the prevention of damaging ophthalmic tissue.

Examples 8 includes the subject matter of Examples 6 and/or 7 and, optionally, wherein the modulating is performed during application of the ultrasound energy to the ophthalmic tissue.

Example 9 includes the subject matter of any one or more of the examples 1 to 8 and, optionally, wherein a characteristic of the ultrasound energy includes one of the following: duration for applying the ultrasound energy, a frequency, a phase, a phase difference, an amplitude, or any combination of the aforesaid.

Example 10 includes the subject matter of any one or more of the examples 1 to 9 and, optionally, wherein the sensor output relates to one of the following of the ophthalmic tissue: temperature, pressure, sound, shear force, strain, vibrations, or any combination of the aforesaid.

Example 11 includes the subject matter of any one or more of the examples 1 to 10 and, optionally, wherein the at least one sensor employs one of the following sensing modalities: fiber-optical sensing; thermal sensing; conductivity measurement sensing; MEMS-based vibration and/or sound sensing; remote sensing, tissue-engaging sensor, or any combination of the aforesaid.

Example 12 includes the subject matter of any one or more of the examples 1 to 11 and, optionally, wherein the sensor provides the sensor output in real-time or near real-time.

Example 13 includes the subject matter of any one or more of the examples 1 to 12 and, optionally, wherein the automatic controlling of the ultrasound transducer is performed in real-time or in near real-time to prevent damage of ophthalmic tissue.

Example 14 includes an intraoperative ophthalmic tissue monitoring system configured for employment during phacoemulsification of a mammalian's eye lens, the system comprising: at least one sensor configured to sense one or more physical quantities to which ophthalmic tissue is subjected to due to the application ultrasound energy for performing phacoemulsification of the lens and wherein the sensor is further configured to provide a sensor output relating to the sensed physical quantity; a processor, and a memory comprising for storing software executable by the processor for enabling the following: determining, based on the sensor output, whether an alert criterion is met for outputting an alert to prevent damage of the ophthalmic tissue due to the application of ultrasound energy to the lens.

Example 15 includes the subject matter of example 14 and, optionally, wherein the ophthalmic tissue is the mammalian's cornea of the same eye.

Example 16 includes the subject matter of example 15 and, optionally, outputting information related to the sensor output such that a user can control a characteristic value of ultrasound energy, based on the output information.

Example 17 includes the subject matter of any one or more of the examples 14 to 16 and, optionally, wherein a position of the sensor relative to the ophthalmic tissue is independent of a position of a phacoemulsification device employed for applying the ultrasound energy.

Example 18 includes the subject matter of any one or more of the Examples 14 to 17 and, optionally, automatically controlling an output of the phacoemulsification device based on the sensor output.

Example 19 includes the subject matter of any one or more of the examples 14 to 18 and, optionally, wherein when an alert criterion is met, a user control input provided by the user for controlling the phacoemulsification device is overridden by a system control input provided to prevent inadvertently inflicting damage to ophthalmic tissue by the phacoemulsification device. For example, the system control input takes precedence over the user control input.

Example 20 pertains to an intraoperative ophthalmic tissue monitoring method, comprising: sensing, by at least one sensor, a physical quantity relating to an ophthalmic tissue characteristic of an eye,_providing, responsive to sensing the physical quantity, a sensor output relating to the sensed physical quantity, controlling by a processor and a memory, based on the sensor output, a characteristic of ultrasound energy for performing phacoemulsification of a lens of the eye.

Example 21 pertains to an intraoperative ophthalmic tissue monitoring method, comprising, during phacoemulsification an eye's lens: sensing one or more physical quantities to which ophthalmic tissue is subjected to due to the application ultrasound energy for performing phacoemulsification of the lens; providing a sensor output relating to the sensed physical quantity; determining, based on the sensor output, whether an alert criterion is met for outputting an alert to prevent damage of the ophthalmic tissue due to the application of ultrasound energy.

What is claimed is:

1. An intraoperative ophthalmic tissue monitoring system, comprising:

at least one measurement sensor configured to sense a physical quantity of an ophthalmic tissue of an eye, at least one reference sensor configured to sense a characteristic of an ultrasound energy that is output by the tip of a phacoemulsification device;

a processor, and a memory comprising for storing software executable by the processor for enabling the following:

providing, based on the at least one measurement sensor, a measurement sensor output relating to the sensed physical quantity;

providing, based on the at least one reference sensor, a reference sensor output relating to the sensed characteristic of the ultrasound energy that is output by the tip; and controlling, based on the measurement sensor output and the reference sensor output, the characteristic of the ultrasound energy configured for performing phacoemulsification of a lens of the eye by the tip of the phacoemulsification device for preventing applying excess ultrasound energy.

2. The intraoperative ophthalmic tissue monitoring system of claim 1, further comprising:

displaying information related to the measurement sensor output and the reference sensor output; and controlling, based on the displayed information, a value of the characteristic of the ultrasound energy.

3. The intraoperative ophthalmic tissue monitoring system of claim 2, wherein the measurement sensor output and the reference sensor output are configured to be processed for displaying to a medical professional and/or for controlling the characteristic of the ultrasound energy to be applied to the lens.

4. The intraoperative ophthalmic tissue monitoring system of claim 1, comprising:

providing, based on the measurement sensor output and the reference sensor output, control feedback to enable automatic control of the phacoemulsification device.

5. The ophthalmic tissue monitoring system of claim 1, wherein the processor is configured for determining whether the measurement sensor output and the reference sensor output meet one or more criteria for displaying an alert.

6. The ophthalmic tissue monitoring system of claim 1, wherein the processor is configured for determining whether the measurement sensor output and the reference sensor output meet one or more criteria for modulating a value of the characteristic of the ultrasound energy to be applied to the lens.

7. The ophthalmic tissue monitoring system of claim 5, wherein the one or more criteria pertain to a prevention of damaging the ophthalmic tissue.

8. The ophthalmic tissue monitoring system of claim 6, wherein the processor is configured for modulating a value of the characteristic of the ultrasound energy.

9. The intraoperative ophthalmic tissue monitoring system of claim 1, wherein the characteristic of the ultrasound energy includes one of the following: duration for applying the ultrasound energy, power, a frequency, a phase, a phase difference, an amplitude, or any combination of the aforesaid.

10. The intraoperative ophthalmic tissue monitoring system of claim 1, wherein the measurement sensor output and the reference sensor output relate to one of the following of the ophthalmic tissue:

temperature, pressure, shear force, strain, vibrations, or any combination of the aforesaid.

11. The intraoperative ophthalmic tissue monitoring system of claim 1, wherein the at least one measurement sensor and/or at least one reference sensor employs one of the following sensing modalities:

fiber-optical sensing; thermal sensing; conductivity measurement sensing; MEMS-based vibration and/or sound sensing; remote sensing, tissue-engaging sensor, or any combination of the aforesaid.

12. The intraoperative ophthalmic tissue monitoring system of claim 2, wherein the controlling and the displaying is performed in real-time or in near real-time to prevent damage to the ophthalmic tissue.

13. The intraoperative ophthalmic tissue monitoring system of claim 1, further configured to perform the following:

determining, based on the measurement sensor output, whether an alert criterion is met for outputting an alert to prevent damage of the ophthalmic tissue due to an application of the ultrasound energy to the lens.

14. The intraoperative ophthalmic tissue monitoring system of claim 13, wherein, when the alert criterion is met, a user control input configured to be provided by the user is overridden by a system control input which is output to prevent inadvertently inflicting damage to the ophthalmic tissue.

15. The intraoperative ophthalmic tissue monitoring system of claim 1, wherein the ophthalmic tissue is a cornea.

16. The intraoperative ophthalmic tissue monitoring system of claim 15, further comprising:

providing output information related to the measurement sensor output and the reference sensor output; and controlling, based on the output information, a value of the characteristic of the ultrasound energy.

17. The intraoperative ophthalmic tissue monitoring system of claim 1, wherein a position of the measurement sensor relative to the ophthalmic tissue is independent of a position of the phacoemulsification device employed for applying the ultrasound energy.

18. The intraoperative ophthalmic tissue monitoring system of claim 1, wherein the measurement sensor is physically decoupled from a position of the phacoemulsification device.

19. The intraoperative ophthalmic tissue monitoring system of claim 18, wherein the measurement sensor is configured to be physically disengaged from the ophthalmic tissue.

20. A method for intraoperatively monitoring ophthalmic tissue during phacoemulsification performed by a phacoemulsification device, the method comprising:

providing, based on at least one measurement sensor, a measurement sensor output relating to a sensed physical quantity relating to an eye;

providing, based on at least one reference sensor, a reference sensor output relating to a sensed characteristic of an ultrasound energy that is output by a tip of the phacoemulsification device; and controlling, based on the measurement sensor output and the reference sensor output, the characteristic of the ultrasound energy for performing phacoemulsification for preventing applying excess ultrasound energy output.

* * * * *